United States Patent [19]

Riall

[11] Patent Number: 5,582,222
[45] Date of Patent: Dec. 10, 1996

[54] BOTTLE CLOSURE MECHANISM USING A SLIDING SHUTTER

[75] Inventor: James D. Riall, Pittsford, N.Y.

[73] Assignee: Johnson & Johnson Clinical Diagnostics, Inc., Rochester, N.Y.

[21] Appl. No.: 412,423

[22] Filed: Mar. 29, 1995

[51] Int. Cl.[6] ..................................... B01L 9/00
[52] U.S. Cl. .................. 141/346; 141/326; 222/144.5; 211/76; 422/102; 422/104
[58] Field of Search ........................ 141/346, 323, 141/326, 354, 355, 367; 222/129, 136, 144.5, 555, 561; 211/76; 215/329, 335; 220/523, 524, 525; 206/446; 422/102, 104; 239/303, 304, 308; 128/200.18

[56] References Cited

U.S. PATENT DOCUMENTS

| | | | |
|---|---|---|---|
| 2,159,978 | 5/1939 | Parkin | 222/561 |
| 2,554,444 | 5/1951 | Koeppel | 222/555 |
| 2,878,829 | 3/1956 | Folmsbee | 137/588 |
| 3,337,082 | 8/1967 | Dorgelys | 211/76 |
| 4,224,958 | 9/1980 | Kaplan et al. | 137/340 |
| 4,844,872 | 7/1989 | Geiselman et al. | 422/100 |
| 5,322,668 | 6/1994 | Tomasso | 422/104 |
| 5,398,846 | 3/1995 | Corba et al. | 222/136 |

*Primary Examiner*—Renee S. Luebke
*Assistant Examiner*—Steven O. Douglas
*Attorney, Agent, or Firm*—Dana M. Schmidt

[57] ABSTRACT

There is disclosed a closure mechanism for two reagent bottles in a bottle holder of an analyzer, using a shutter that slideably and frictionally engages the top surface of grommets at the mouth of the bottles. The shutter slides to either an open or closed position of the bottles, either both in lock-step or with one bottle open, the other closed, and both closed together. The shutter is driven by a cam and cam followers, either rotationally or linearly.

11 Claims, 4 Drawing Sheets

BOTTLE CLOSURE MECHANISM USING A SLIDING SHUTTER

FIELD OF THE INVENTION

This invention relates to a closure mechanism for plural reagent bottles in a bottle holder, such as is used in a clinical analyzer.

BACKGROUND OF THE INVENTION

Analyzers (so-called wet assay analyzers) supply liquid reagents in bottles. These bottles, though initially closed off, are necessarily penetrated by aspirator probes when reagents are needed. Such repeated penetrations produce substantial degradation to the reagents for the following reasons: first, it has been practically impossible to reseal the bottle after the first penetration. Attempts to avoid this have used such things as penetrable septums that are supposed to reseal after penetration, but repeated penetration more or less along the same line produces "coring" which leaves a permanent air passage in the septum, air degradation of the reagent and residual deposits of the reagent on the seal which can create carry-over and growth of molds. Alternatively, penetration of the septum causes a second problem, namely deposit of septum material into the reagent liquid being stored, and this, in turn, can degrade the reagent. Although this second problem is lessened by using seals such as "duck-bill" seals, those still have the first problem, namely inadequate resealing against air contamination.

The problem then that has long faced the wet assay analyzer is how to provide on- analyzer keeping of the liquid reagents more than one or two weeks, without having to constantly replace the bottles. That is, how can a large quantity of reagent be kept on-analyzer, for one or two months, without degradation due to contact with ambient air (evaporation) or foreign materials?

SUMMARY OF THE INVENTION

We have designed a closure of reagent bottles, since it is in fact a closure problem, that solves the aforesaid long-standing need. More specifically, in accord with the invention there is provided a combination comprising a bottle holder and a first and second bottle of liquid in the holder, each bottle comprising a container with an open mouth, the holder comprising support walls constructed to hold the bottles, a grommet having a through-aperture and disposed by the support walls at the mouth of each the container so as to close off the mouth except for the through-aperture, and a closure means for opening and closing the grommet apertures, and hence the container mouth, on demand, the closure means comprising a shutter, means in the bottle holder for mounting the shutter for sliding movement, in contact with and relative to the grommets, between a first and a second position, one of the positions being that which closes off at least one of the grommet apertures and the other of the positions that which opens the at least one grommet aperture, the shutter further including at least one sealing lobe shaped and sized to close off a grommet aperture when the shutter lobe is in one of the positions, the lobe being operatively disposed so as to move into and out of the positions in response to movement of the shutter.

Accordingly, it is an advantageous feature of the invention that reagent bottles can be stored on-analyzer for much longer than has been heretofore possible, even for months, without degradation.

It is a related advantageous feature that such storage is possible using a closure mechanism that is simple in construction, and yet ensures reclosure after each usage without contaminating the bottle with foreign material, and without contacting the seal with bottle reagent.

Other advantageous features will become apparent upon reference to the following detailed description when read in light of the attached drawings.

DESCRIPTION OF THE PREFERRED EMBODIMENTS

Figure 1:
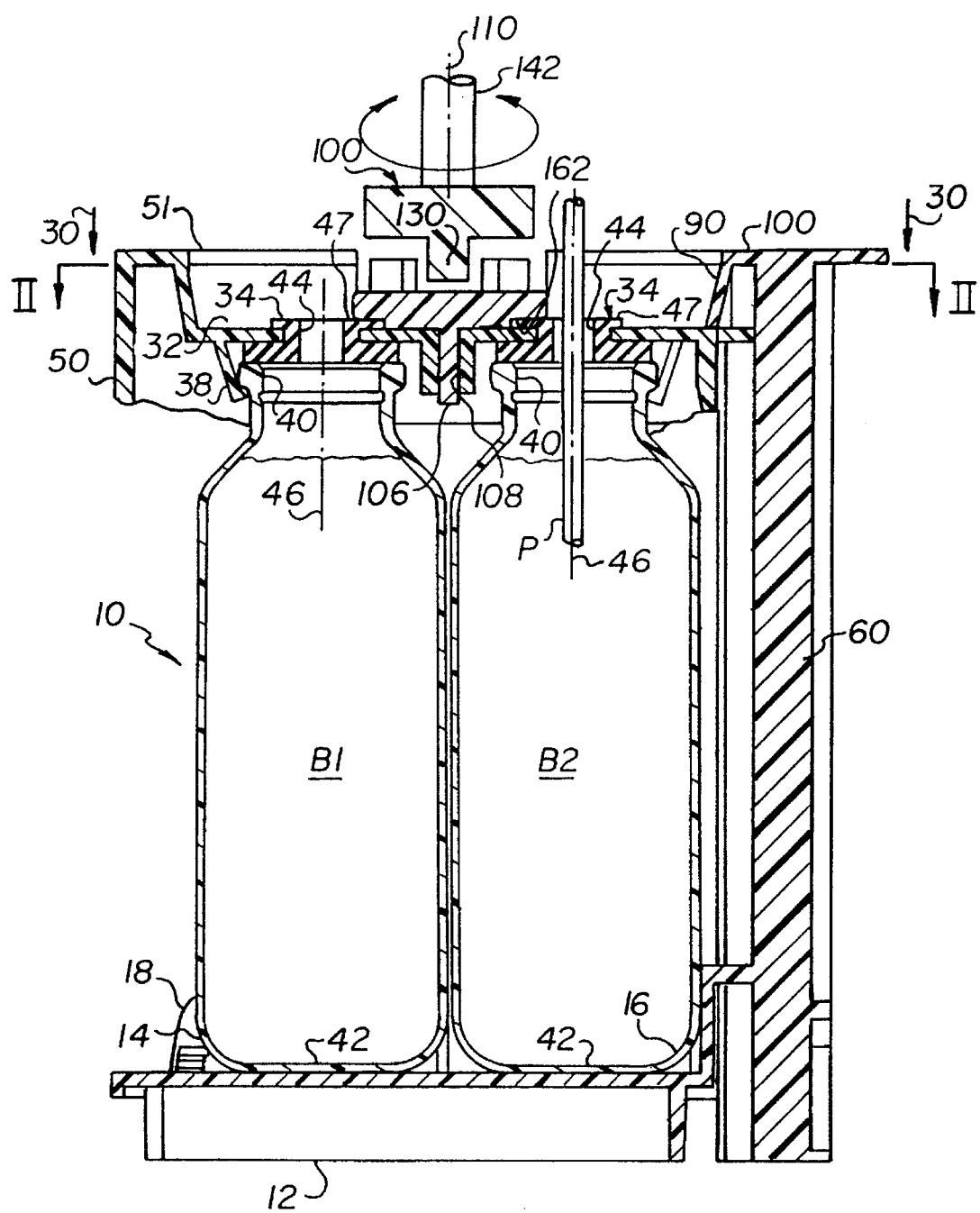
FIG. 1 is a side elevational view in section of the combination of the invention when used with a preferred bottle holder, showing the shutter mechanism in its open position.

The invention is hereinafter described in connection with certain preferred embodiments, in which bottles of a preferred form are mounted in pairs in a preferred holder and a closure mechanism is mounted there-above to rotate about an axis that is in a preferred angular orientation with respect to the bottles. In addition, the invention is useful regardless of the form of the bottles, so long as they are open-mouth bottles, whether they are in pairs or other numbers, and regardless of the form of the holder and whether the closure mechanism moves by rotation or some other mechanism. If rotation is used, the invention is also applicable regardless of the particular angular positioning of the axis of rotation with respect to the bottles present.

Orientations such as "above", "below", "top", "side" and the like refer to the orientation of the parts in their intended use.

Thus, a preferred bottle holder for use in the combination is that described in U.S. Pat. No. 5,322,668. Such a holder 10 is generally pie-shaped, FIG. 2, so as to slide in and out of a wet chemistry analyzer, as is conventional (not shown), generally in a circular arrangement of such holders. Such a bottle holder 10 comprises, FIG. 1, a base 12, a top member 30, and a sidewall 60 extending between and joined to the base and top member.

More precisely, base 12 comprises a platform having at lest one recess and preferably recesses 14 and 16, for each of two open mouth bottles B1 and B2 held by holder 10. As is apparent, recesses 14 and 16 are disposed along the length of holder 10, which is the dimension that aligns with a radius of the circular arrangement of such holders in the analyzer (not shown). Recess 14 is partially defined by an upstanding lug 18. Recess 16 is preferably defined by raised sidewalls.

Base 12 is joined to side wall 60 by any conventional means, e.g. by welding, by adhesive, by mechanical latches, etc. Bottles B1 and B2 preferably hold two different reagent solutions.

Top member 30 comprises a generally flat plate 32 provided with grommets 34, and depending fingers 36 with snap latches 38 for locking under the rim of the mouth 40 of a bottle B1 or B2 with each grommet 34 in contact with a mouth 40. (Opposite ends 42 of the bottles are retained in recesses 14 and 16). Apertures 44 in grommets 34 are generally aligned with a center axis 46 of each of mouths 40. Each grommet has an exposed exterior surface 47. A side skirt 50 wraps partially around plate 32 and engages wall 60 using teeth 90.

Figure 2:
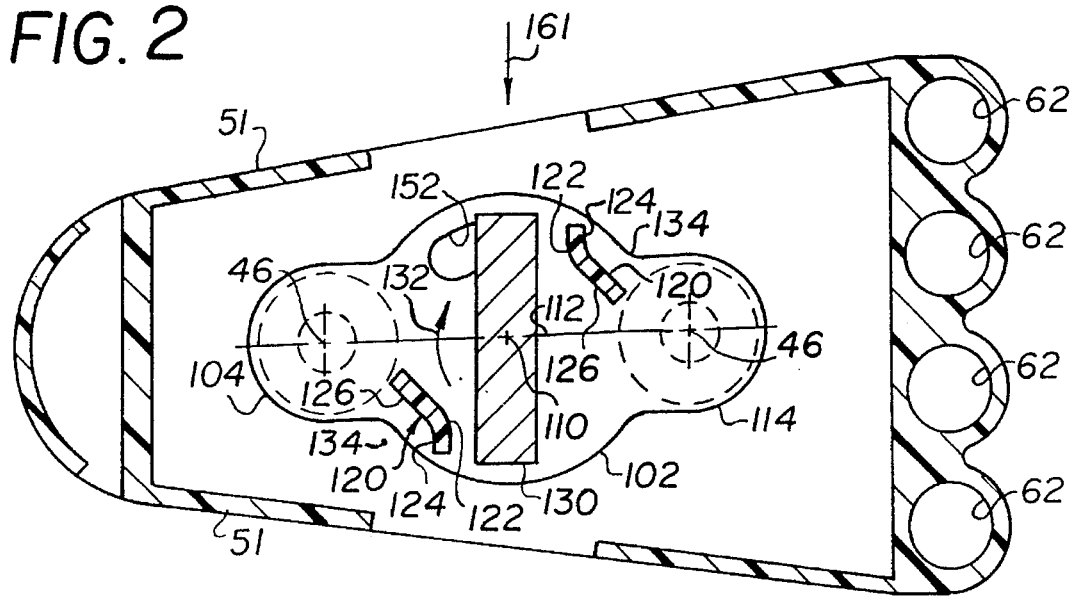
FIG. 2 is a section view taken generally along the line II—II of FIG. 1, except that the shutter has been rotated to its closed position.

Sidewall 60 can have any desired shape and thickness, but preferably it has a plurality of, e.g., four cylindrical apertures 62, FIG. 2, extending the full height of the wall. A stack of reaction cuvettes, not shown, preferably is mounted within each aperture. The cuvettes are preferably shaped as cups or wells. They nest one inside the other, and the uppermost cuvette is preferably topped with a seal cap to seal off the stack from the atmosphere. The bottom of the stack is sealed within the aperture 62 by virtue of a friction fit between a flange of each cuvette, and the sidewall of the aperture 62.

In accordance with the invention, a closure means 100 is provided for apertures 44, that avoids the problems noted above for prior bottle holders. Means 100 preferably comprises a shutter 102, FIG. 2, having at least one sealing lobe 104 that actively engages one of the grommets 34 (for bottle B1), and cam 120 on the lobe, a cam 130 mounted to engage and disengage the cam follower, and means 150, FIG. 1, for activating cam 130.

Figure 3:
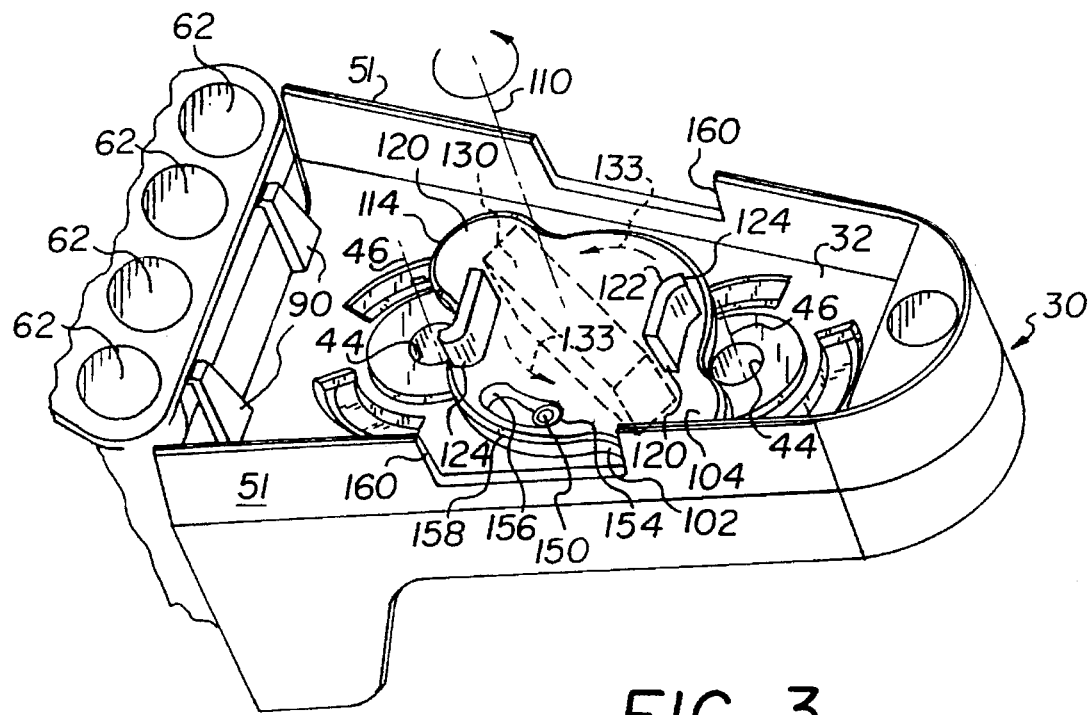
FIG. 3 is a fragmentary perspective view of the combination shown in FIG. 1, from the opposite side, and with the activating cam in phantom only.

Considering first the shutter 102, it includes a stud 106 that is journalled within an opening 108 of cover 30, so that stud 106 and shutter 102 are preferably positioned, FIGS. 2-3, for rotation about an axis 110 which is preferably substantially aligned with, or on, a line 112, extending from the approximate centers of mouths 44 of the grommets as determined by axes 46.

More specifically, preferably shutter 102 includes a second lobe 114 as well as first lobe 104. In the embodiment of FIGS. 1-4, lobe 114 is disposed 180° about axis 110, to actively engage the other grommet 44 (for bottle B2), FIG. 2. By "actively engage", what is meant herein is preferably a sliding movement of each lobe in frictional contact with the exterior surface 47 of the respective grommet, FIG. 1. In this manner, the shutter via its lobes opens and closes access to the interior of the grommet and therefore its respective bottle. Because lobes 104 and 114 are 180° apart, about axis 110, and because axis 110 is substantially on lines 112, both grommets and bottles B1,B2 end up being open at the same time, FIG. 3, and closed at the same time, FIG. 2, as will be readily apparent.

Cam followers 120 are provided, one for each lobe. Preferably they have an L-shape with an inner corner 122, and a shorter leg 124, a longer leg 126, extending from the corner. It is these legs 124,126 that are engaged by the cam 130, as shown in phantom, to force shutter 102 to rotate open, arrow 132, or closed, arrows 133, FIG. 3.

Alternatively, cam followers can have other shapes, for example, that of a 90° arc about an imaginary center 134, FIG. 2.

Cam 130, in turn, is driven by a suitable means 140, such as a drive shaft 142, FIG. 1, operated by a conventional stepper motor (not shown). Alternatively, cam 130 can be rotated by a pulley or by a rack and pinion gear (not shown) with the pinion gear being located on the shaft 142.

Figure 4:
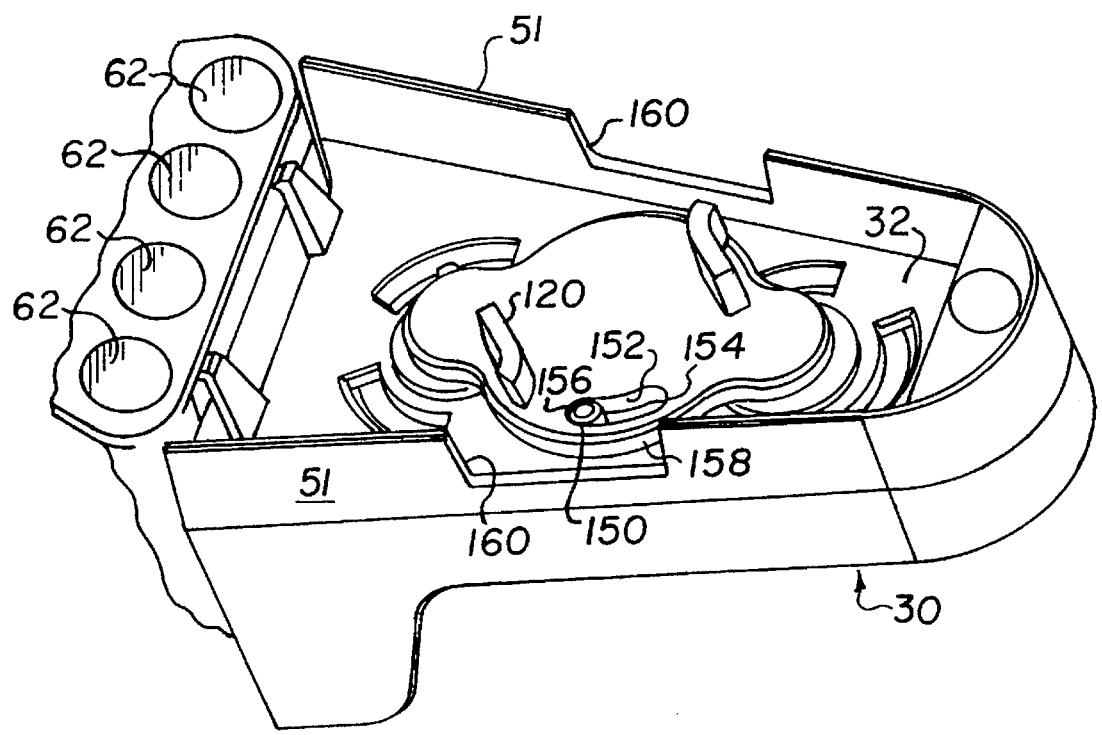
FIG. 4 is a view similar to that of FIG. 3, but of the shutter rotated into its closed position as shown in FIG. 2.

To further guide shutter 102 on its rotational movement, a stop pin 150 preferably extends fixedly from the top surface 32 of cover 30, FIGS. 3 and 4. This cooperates with a slot or groove 152 formed in shutter 102, the slot 152 having two opposed ends 154, 156 that cooperate with stop pin 150 to prevent over-rotation in either the open position, FIG. 3, or the closed position, FIG. 4

Alternatively, slot 152 need not be completely enclosed within shutter 102. Instead, portion 158 which completely encloses pin 150 can be removed along the dotted lines FIG. 4.

As noted above, skirt 50 is only partially wrapped around to provide upstanding shoulders 51. That is, a cut-out 160 is provided in shoulders to allow access of cam 130 to the cam followers without raising the cam and lowering it—arrow 161, FIG. 2.

As is readily apparent, when shutter 102 is in the position shown in FIGS. 1 and 3, an aspirator probe P can be inserted by the analyzer in which holder 10 is placed, to aspirate out some of the contents of either bottle (shown as B2 in FIG. 1).

It has been further determined that optimal performance in the active engagement of grommets 34 by shutter 102, occurs when the following materials are utilized:

Grommets 34 preferably comprise an elastomer that provides a hardness of at least about 45 durometers Shore A, is inert to the contents of bottles B1 and B2, does not outgas, deforms slightly without taking a "set", as is known in the art, and is non-sticky, that is, has a coefficient of friction of no greater than about 0.5 when engaged with a polypropylene or polyethylene shutter 102. Thus, hardnesses of 45, 60 and 75 durometers Shore A are considered useful, with 45 being most preferred. Any elastomer meeting these conditions will suffice. Most preferably, the elastomer of choice is a silicone—modified thermoplastic elastomer such as that available under the trade name "C-Flex R70-081" from Concept Polymer Tech. Another useful example is a polypropylene EPDM elastomer available under the trade name "Vista-flex" from Advanced Elastomer Systems.

As will be readily apparent from the foregoing, the material of at least the under-surface 162 of shutter 102, FIG. 1, in contact with grommets 34, is preferably polypropylene or polyethylene. In addition, other polymeric materials providing a very low moisture-vapor transmissibility (leakage) through the contacting under-surface 162, can be used, provided they also provide the same order of coefficient of frictional engagement with the grommet material as described above.

It is not essential that the lobes of shutter 102 open and close both bottles simultaneously. Alternatively, shutter 102 can be constructed to open one at a time, and close both together, FIGS. 5-7. Parts similar to those previously described bear the same reference numerals, to which the distinguishing suffix "A" has been appended.

Figure 5:
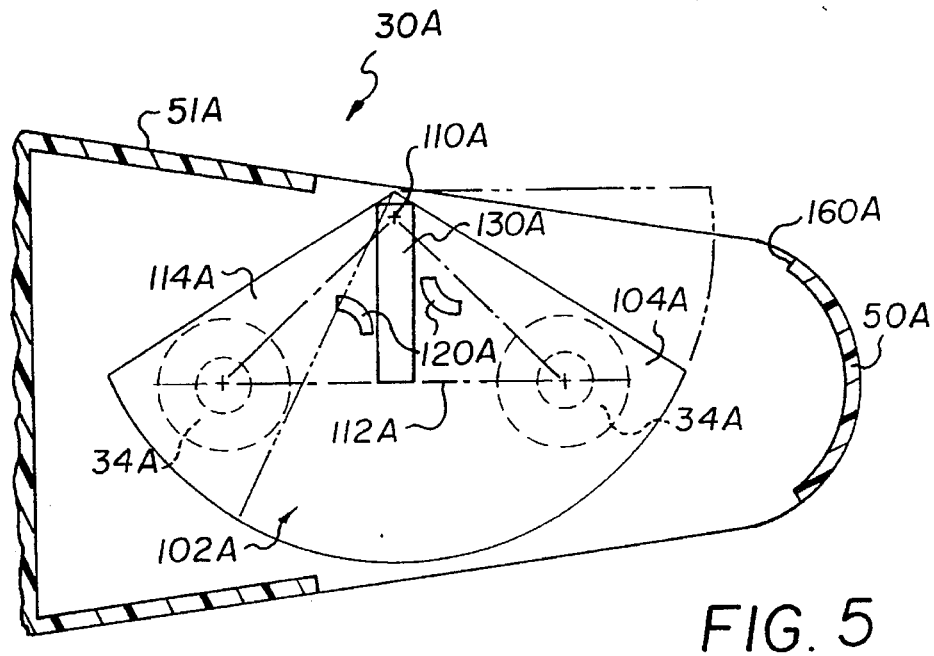
FIG. 5 is a plan view in section similar to that of FIG. 2, but of an alternate embodiment.

Thus, FIG. 5, cover 30A has a skirt 50A, grommet 34A shown in phantom, and shutter 102A pivoted about an axis 110A by a cam 130A acting on cam followers 120A disposed on respective lobes 104A and 114A of shutter 102A, as before. However, in this embodiment, lobes 104A and 114A are disposed rotationally approximately 90° about axis 110A, and said axis is moved substantially away from line 112A connecting the approximate centers of grommets 34A.

More precisely, axis 110A is located near one of the shoulders 51A formed by skirt 50A. Cut-outs 160A are then disposed to allow either lobe 104A or lobe 114A to move therethrough (shown in phantom), depending on which side (skirt 51A) axis 110A is located next to.

Figure 6:
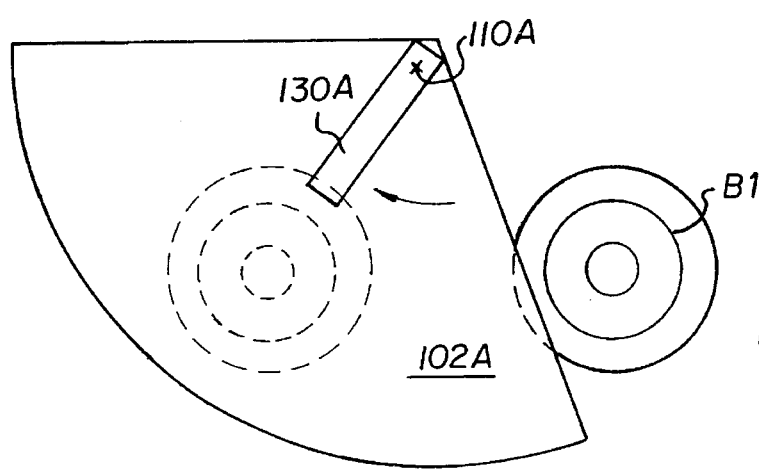
FIGS. 6 and 7 are schematic plan views showing the operation of the embodiment of FIG. 5 so that either bottle, but not both, is open for access.
Figure 7:
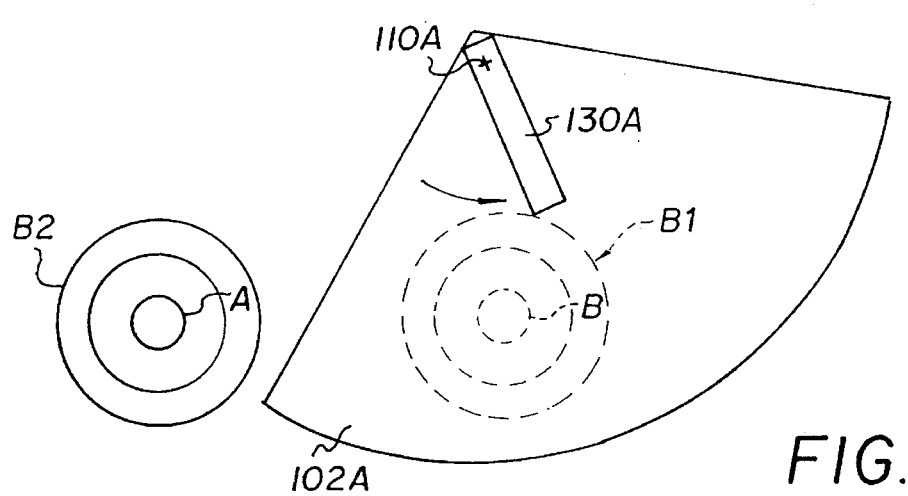

As is schematically illustrated in the three figures, this construction allows shutter 102A to either close both grommets (of both bottles),.as shown in solid on FIG. 5, to open only the grommet of bottle B1, FIG. 6, or to open only the grommet of bottle B2, FIG. 7, as actuated by cam 130A being rotated about axis 110A.

Figure 8:
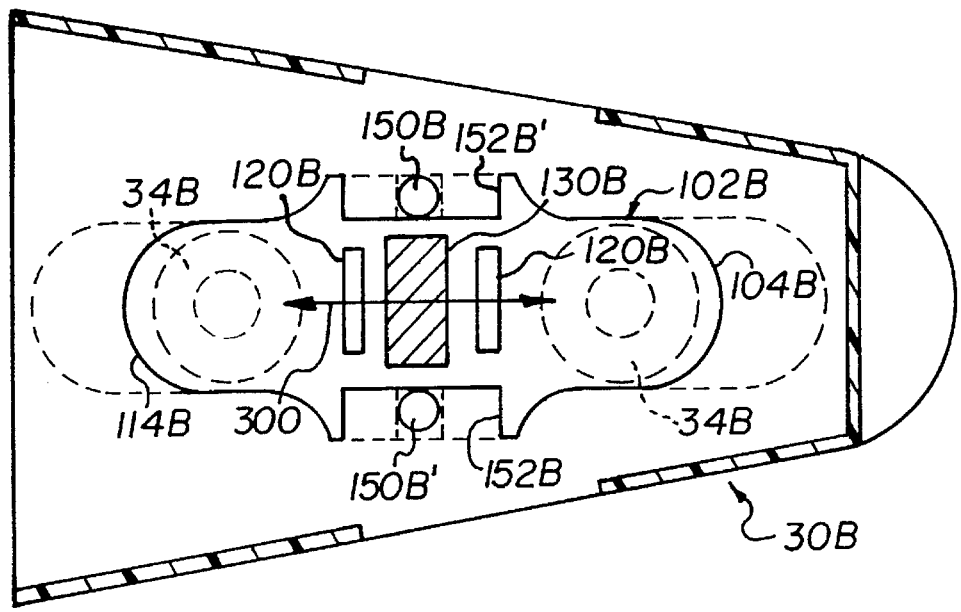
FIG. 8 is a plan view similar to that of FIG. 5, but of yet another embodiment.

Still further, there is no need for the sliding engagement of shutter 102 or 102A to be one of rotation against the grommets. Linear translation is also useful, as is shown in FIG. 8. Parts similar to those previously described bear the same reference numeral to which the distinguishing suffix "B" is appended.

Thus, cover 30B has mounted therein grommets 34B which slideably and frictionally engage a shutter 102B comprising two lobes 104B, 114B, each with a cam followers 120B engaged by a cam 130B, shutter 102B being restrained by stop pin 150B, as in the previous embodiments. However, shutter 102B in this case is driven only linearly, arrow 300, in accordance with the linear movement of cam 130 (as driven, for example, by a rack and pinion gear (not shown) the rack gear being affixed to cam 130A). An additional stop pin 150A' is added, along with additional slot 152B'. The result is that the grommets are both closed off, as shown in solid, or one or the other is opened, as shown by the 2 phantom positions of the respective lobes.

The invention disclosed herein may be practiced in the absence of any element which is not specifically disclosed herein.

The invention has been described in detail with particular reference to preferred embodiments thereof, but it will be understood that variations and modifications can be effected within the spirit and scope of the invention.

What is claimed is:

1. A combination comprising a bottle holder and a first and second bottle of liquid in the holder, each bottle comprising a container with an open mouth, said holder comprising support walls constructed to hold said bottles, a grommet having a through-aperture and disposed by said support walls at the mouth of each said container so as to close off said mouth except for said through-aperture, and a closure means for opening and closing said grommet apertures, and hence the container mouth, on demand;

said closure means comprising a shutter, means in said bottle holder for mounting said shutter for sliding movement, in contact with and relative to said grommets, between a first and a second position, one of said positions being that which closes off at least one of said grommet apertures and the other of said positions that which opens said at least one grommet aperture, said shutter further including at least one sealing lobe shaped and sized to close off a grommet aperture when said shutter lobe is in one of said positions, said lobe being operatively disposed so as to move into and out of said positions in response to movement of said shutter.

2. A combination as defined in claim 1, wherein said closure means further comprises a cam follower on said shutter, a cam mounted for movement above said shutter into and out of contact with said cam follower, and means for moving said cam into and out of said contact.

3. A combination as defined in claim 1, wherein said mounting means for said shutter is constructed to mount said shutter for linear translation between said positions.

4. A combination as defined in claim 1, wherein said mounting means for said shutter is constructed to mount said shutter for rotation about an axis between said positions.

5. A combination as defined in claim 4, wherein said cam is mounted for rotation about said axis.

6. A combination as defined in claim 4, wherein said shutter comprises two lobes angularly disposed from each other about said rotational axis so that one is 90° from the other, and said axis is located substantially away from a line extending between the approximate centers of said grommet apertures, so that when one grommet aperture is closed by one of said lobes, the other can be open.

7. A combination as defined in claim 4, wherein said shutter comprises two lobes angularly disposed from each other about said rotational axis so that one is 180° from the other, and said axis is located substantially on a line extending between the approximate centers of said grommet apertures, so that one grommet aperture is closed by one of said lobes, the other is also closed.

8. A combination as defined in claim 4, wherein said axis is located outside of a line drawn between the approximate centers of said grommet apertures.

9. A combination as defined in claim 1, wherein said grommet apertures are preformed so that they do not produce particles that fall into said reagent upon penetration by an aspirator.

10. A combination as defined in claim 1, wherein each of said grommets comprise an elastomer that provides a hardness of at least about 45 durometers Shore A, is inert to the contents of said bottles, does not outgas, deforms slightly without taking a "set", and has a coefficient of friction no greater than about 0.5 when engaged by said shutter comprising polypropylene or polyethylene.

11. A combination as defined in claim 10, wherein said grommets comprise a silicone-modified thermoplastic elastomer.

* * * * *